United States Patent [19]
Golds

[11] Patent Number: 5,356,417
[45] Date of Patent: Oct. 18, 1994

[54] ABSORBABLE STERNUM CLOSURE BUCKLE

[75] Inventor: Ellen Golds, Hastings-on-Hudson, N.Y.

[73] Assignee: United States Surgical Corporation, Norwalk, Conn.

[21] Appl. No.: 959,165

[22] Filed: Oct. 9, 1992

[51] Int. Cl.$^5$ .............................................. A61B 17/00
[52] U.S. Cl. ...................................... 606/151; 606/74; 24/16 PB
[58] Field of Search ............... 606/151, 157, 191, 213, 606/215, 216, 218; 24/16 PB, 30.5 P, 194

[56] References Cited

U.S. PATENT DOCUMENTS

| | | |
|---|---|---|
| 1,717,766 | 6/1929 | Eimler . |
| 1,950,799 | 3/1934 | Jones . |
| 2,622,292 | 12/1952 | Pehaczek . |
| 2,948,939 | 8/1960 | Prete, Jr. . |
| 2,987,062 | 6/1961 | Ellison . |
| 3,111,945 | 11/1963 | von Solbrig . |
| 3,469,573 | 9/1969 | Florio . |
| 3,473,528 | 10/1969 | Mishkin et al. . |
| 3,494,002 | 2/1970 | Kabel ................... 24/16 PB |
| 3,570,497 | 3/1971 | Lemole . |
| 3,577,601 | 5/1971 | Mariani et al. . |
| 3,798,711 | 3/1974 | Cousins . |
| 3,802,438 | 4/1974 | Wolvek . |
| 4,035,877 | 7/1977 | Brownson et al. . |
| 4,037,603 | 7/1977 | Wendorff . |
| 4,069,554 | 1/1978 | Minolla et al. . |
| 4,119,091 | 10/1978 | Partridge . |
| 4,136,422 | 1/1979 | Ivanov et al. . |
| 4,201,215 | 5/1980 | Crossett et al. . |
| 4,208,770 | 6/1980 | Takada . |
| 4,263,904 | 4/1981 | Judet . |
| 4,279,248 | 7/1981 | Gabbay . |
| 4,371,192 | 2/1983 | Alix . |
| 4,386,452 | 6/1983 | Stephenson . |
| 4,387,489 | 6/1983 | Dudek . |
| 4,428,376 | 1/1984 | Mericle ................... 606/154 |
| 4,512,346 | 4/1985 | Lemole . |
| 4,535,764 | 8/1985 | Ebert . |
| 4,551,889 | 11/1985 | Narayan et al. . |
| 4,583,541 | 4/1986 | Barry . |
| 4,608,735 | 9/1986 | Kasai . |
| 4,625,717 | 12/1986 | Covitz . |
| 4,643,178 | 2/1987 | Nastari et al. . |
| 4,712,280 | 12/1987 | Fildan . |
| 4,730,615 | 3/1988 | Sutherland et al. . |
| 4,791,709 | 12/1988 | Fildan . |
| 4,792,336 | 12/1988 | Hlavacek et al. . |
| 4,802,477 | 2/1989 | Gabbay . |
| 4,813,416 | 3/1989 | Pollak et al. . |
| 4,825,515 | 5/1989 | Wolterstorff, Jr. . |
| 4,826,250 | 5/1989 | Ibanez . |
| 4,878,271 | 11/1989 | Kitokovsky . |
| 4,896,668 | 1/1990 | Popoff et al. . |
| 4,944,753 | 7/1990 | Burgess et al. . |
| 4,955,913 | 9/1990 | Robinson . |
| 4,966,600 | 10/1990 | Songer et al. . |
| 5,023,980 | 6/1991 | Thomas . |
| 5,123,153 | 6/1992 | Krauss . |
| 5,139,498 | 8/1992 | Ley . |
| 5,163,598 | 11/1992 | Peters et al. . |

FOREIGN PATENT DOCUMENTS 3244680 6/1984 Fed. Rep. of Germany .
9210460 8/1992 France .

*Primary Examiner*—Tamara L. Graysay

[57] ABSTRACT

A strap assembly for surgical repair of split portions of tissue to retain the tissue portion in adjacent contacting relation during healing, which includes an elongated strap member and a buckle member for securing the strap member in a looped tensioned condition about the tissue portions. The buckle member is fabricated from a bioabsorbable material selected from the group consisting of polymers or copolymers of glycolide, lactide, trimethylene carbonate, lactone, dioxanone, and caprolactone. The preferred buckle member includes a housing member defining a longitudinal channel therethrough for reception of the strap member and a wedging member insertable within the longitudinal channel of the housing member to securely wedge the strap member against at least one bearing surface of the housing member.

29 Claims, 5 Drawing Sheets

ABSORBABLE STERNUM CLOSURE BUCKLE

BACKGROUND OF THE INVENTION

1. Field of the Invention

The present invention relates to surgical devices for repair of split portions of tissue. In particular, the invention is directed to a strap assembly for securing a strap about split portions of a sternum to maintain the portions in adjacent contacting relationship during healing.

2. Description of the Prior Art

During surgery that involves a median sternotomy, e.g., open heart surgery, the sternum is split longitudinally to allow access to the organs within the thoracic cavity. Upon completion of the surgery, the sternum is rejoined and closed securely. For proper healing to occur, the split sternum portions are preferably engaged in face-to-face relationship and compressed together while the sternum heals.

Traditional methods for closing a sternum involve securing steel wires around or through the sternum halves and approximating the sternum by twisting the wires together.

Recently, a certain amount of emphasis has been directed towards the use of band or strap assemblies for sternum repair. Such assemblies typically include a locking mechanism which secures a strap in a closed looped configuration about the sternum portions. One example of an assembly of this type is described in U.S. Pat. No. 4,813,416 and includes a banding assembly having a curved surgical needle, an attached thin flat stainless steel band and a buckle mechanism. The sternum halves are brought to abutting closure by looping the band in position around or through the sternum portions and securing the band within the buckle mechanism.

While utilization of steel wires and strap assemblies have been widely accepted for sternum repair, certain shortcomings with these devices are apparent. The use of steel wires presents problems to the surgeon during the operation and to the patient after closure is completed. Steel wires are difficult to maneuver and place around the sternum. The wire edges are often sharp and can easily pierce through undesired areas including tissue surrounding the sternum area or the surgeon's gloves or fingers.

The strap assemblies known heretofore incorporate buckle mechanisms which are relatively structurally complex. For example, the buckle mechanism described in U.S. Pat. No. 4,813,416 includes a saddle part, inturned flanges disposed on opposing sides of the saddle part and a loop segment. The saddle part and inturned flanges define a band slide through course for reception of a portion of the band. A spring leaf extends upwardly from the loop segment through a slot in the saddle part. The tip end of the spring leaf is narrowed to define a spring tooth or projection which projects through an aperture formed in the band to maintain the closed band loop in a locked configuration.

Further, conventional buckle assemblies, such as the type disclosed in U.S. Pat. No. 4,813,416, are fabricated from metal such as stainless steel or the like. The metallic buckle remains within the patient indefinitely after healing has occurred.

Thus, there is a clear need for a surgical device which is simple in construction and effectively secures the divided sternum portions together for healing. There is also a need for a securing device having a buckle which is fabricated from a bioabsorbable material. The present invention is directed to a strap assembly having a bioabsorbable buckle member of relatively simple construction which securably retains a strap in a closed looped locking configuration around sternum portions to maintain the portions in adjacent engaged relation during healing.

SUMMARY OF THE INVENTION

Generally stated, the present invention is directed to a strap assembly for surgical repair of split portions of tissue to retain the tissue portion in adjacent contacting relation during healing, which includes an elongated strap member and buckle means for securing the strap member in a looped tensioned condition about the tissue portions. The buckle means is fabricated from a bioabsorbable material selected from the group consisting of polymers or copolymers of glycolide, lactide trimethylene carbonate, lactone, dioxanone, and caprolactone.

Preferably, the buckle means includes housing means defining a longitudinal channel therethrough for reception of at least a first end portion of the strap member and wedging means insertable within the longitudinal channel of the housing means to securely wedge the strap member against at least one bearing surface of the housing means. The wedging means includes strap engaging means disposed on at least one of an upper or lower surface thereof to facilitate engagement of the strap member.

The strap assembly further includes means for mounting the wedging means within the longitudinal channel of the housing means. Generally, the mounting means includes first and second locking hooks extending from opposed sides of the wedging means, which locking hooks securely engage correspondingly dimensioned and positioned projections extending from opposed sides of the housing means.

In an alternative preferred embodiment, the buckle means includes housing means defining a longitudinal channel extending therethrough and wedging means mounted within the longitudinal channel of the housing means and longitudinally moveable therewithin between a non strap securing position and a strap securing position. The wedging means include strap engaging means disposed on at least one of an upper or lower surface thereof. The strap engaging means is angularly oriented to permit advancement of the strap member in a strap tensioning direction while engaging the strap member when the strap moves through the longitudinal channel in a strap loosening direction. Engagement of the strap member with the strap engaging means during movement of the strap member in the strap loosening direction effects movement of the wedging means to the strap securing position.

The present invention is also directed to a method for repairing split portions of tissue. The method comprises the steps of providing at least one strap assembly including a strap member and buckle means, the buckle means including housing means which define a longitudinal channel for reception of the strap member and wedging means dimensioned to be received within the longitudinal channel, looping a strap member about split portions of tissue, inserting the strap member within the longitudinal channel of the buckle means, tightening the strap in a manner to attach the tissue portions in an adjacent engaged relation and inserting the wedging means within the longitudinal channel of the housing means to securely wedge the strap member against a bearing surface of the housing means.

BRIEF DESCRIPTION OF THE DRAWINGS

Preferred embodiments of the invention will be described hereinbelow with reference to the drawings wherein.

DETAILED DESCRIPTION OF THE PREFERRED EMBODIMENT(S)

Figure 1:
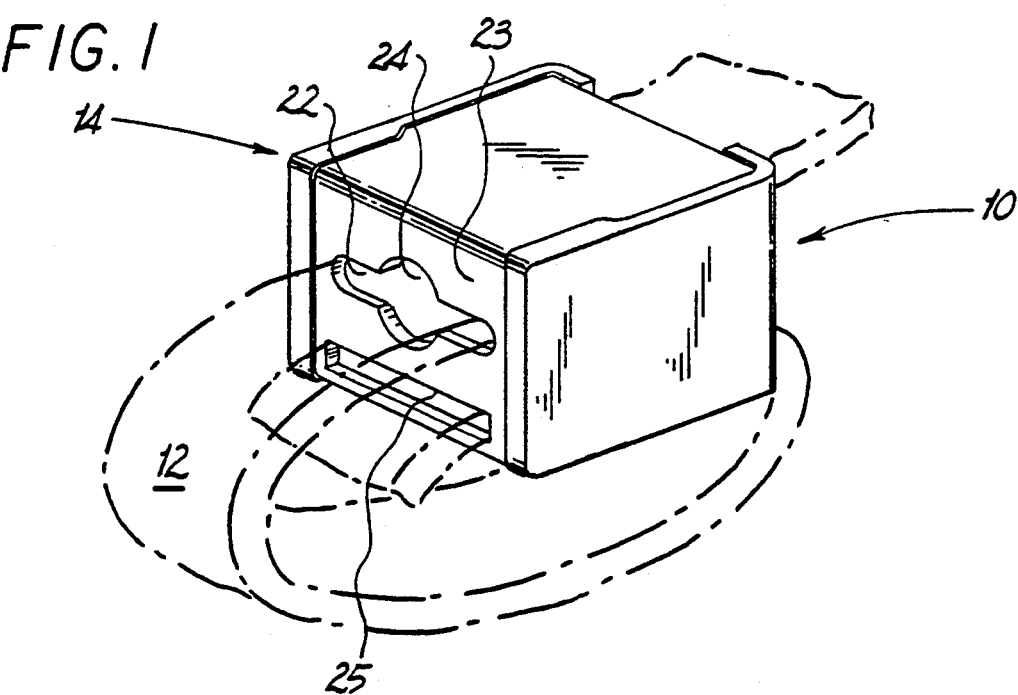
FIG. 1 is a perspective view of the strap assembly constructed according to the present invention illustrating the absorbable buckle member with attached strap.

Referring initially to FIG. 1, there is illustrated an enlarged perspective view of the strap assembly 10 constructed according to the present invention. Strap assembly 10 has particular application in securing split portions of a sternum together after a sternotomy. However, one skilled in the art will readily appreciate other applications for strap assembly 10.

Strap assembly 10 includes elongated strap 12 and buckle member 14. Strap 12 is preferably readily pliable and may be formed of any material suitable for use in stabilizing fractured bones or securing tissue portions together generally. Typically, strap 12 may be fabricated from a wide variety of monofilament and braided materials both absorbable and non-absorbable. Bioabsorbable materials suitable for this use include polymers and copolymers of lactic acid, lactide, glycolic acid, glycolide, dioxanone, caprolactone, trimethylene carbonate and blends thereof, along with various combinations of these materials. Examples of suitable non-absorbable materials include those fabricated from synthetic fibers such as polyesters, polyethylene, polytetrafluoroethylene, polyamides, polycarbonate, polybutylene terephthalate, polyethylene terephthalate, polyvinyl chlorides, polypropylenes and polysulfones.

U.S. patent application Ser. No. 07/829,423, filed Feb. 3, 1992, the contents of which are incorporated herein by reference, discloses a strap or sternum closure ribbon which may be readily adapted for use with the strap assembly 10 of the present invention. The strap disclosed in this application is a braided product having a plurality of elongated filamentary reinforcing members of ultra high molecular weight high tenacity polyethylene fibers. These fibers may be plasma treated to reduce slip characteristics of the yarn and exhibit a strength from about 375 kpsi (thousands of pounds per square inch) to about 560 kpsi and a tensile module from about 15 msi (millions of pounds per square inch) to about 30 msi.

U.S. Pat. No. 5,019,093 to Kaplan et al. which issued on May 28, 1991, the contents of which are also incorporated herein by reference, discloses a suture product which may also be adapted for use with the strap assembly 10 of the present invention. The suture product disclosed in this application is of braided construction and is preferably fabricated from a bioabsorbable polymer such as a glycolide or a lactide. This product exhibits perceptibly enhanced flexibility and hand as well as reduced chatter and drag compared with braided sutures of known construction.

Figure 2:
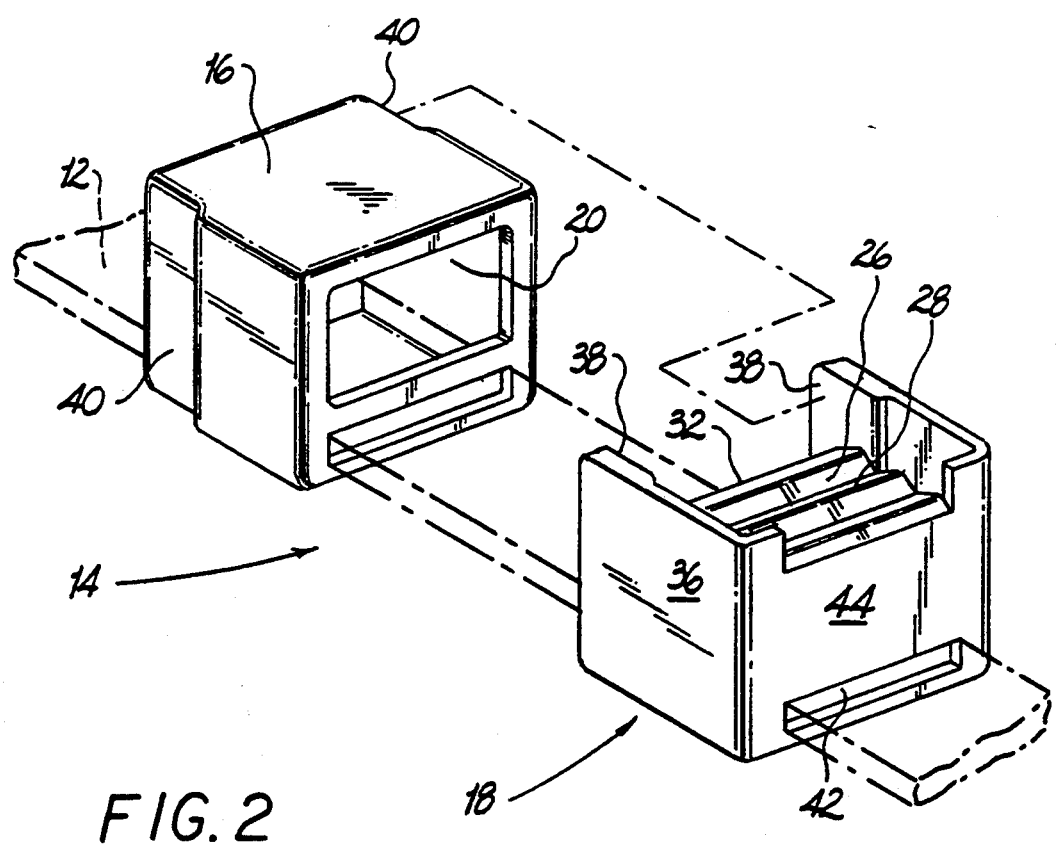
FIG. 2 is a perspective view with parts separated of the buckle member of FIG. 1.
Figure 3:
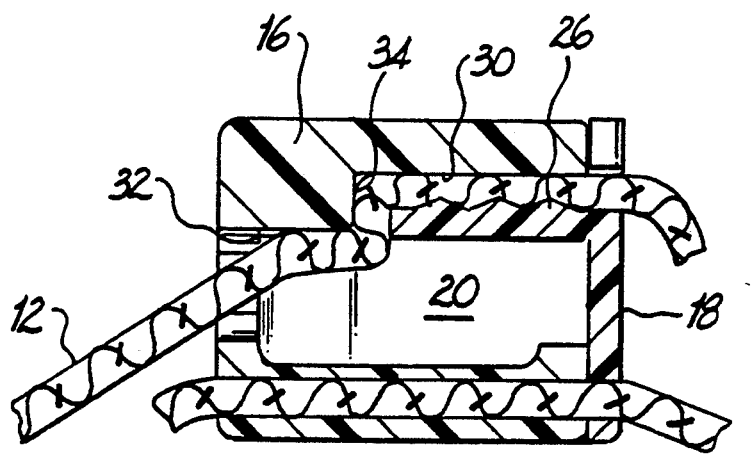
FIG. 3 is a side view in of the buckle member of FIG. 1 with the wedging member mounted within the housing.

Referring now to FIGS. 1–3, buckle 14 is shown in detail so as to illustrate the novel securing mechanism of the present invention. Buckle 14 includes essentially two components, namely, housing member 16 and wedging member 18. Housing member 16 includes longitudinal channel 20 extending therethrough. Housing member 16 also defines a slotted opening 22 on transverse side 23 in general alignment with channel 20. Slotted opening 22 is dimensioned to receive strap 12 which is subsequently passed through channel 20 during the tightening procedure. Slotted opening 22 includes opposed arcuate portions 24 disposed at a mid-portion thereof. Arcuate portions 24 are strategically dimensioned and positioned to accommodate the needled end of the strap during insertion of the strap within slotted opening 22 (see FIG. 4). Housing member 16 also includes a second slotted opening 25 to accommodate a first end portion of the strap, which strap portion is mounted to the housing member by conventional means.

Wedging member 18 is generally U-shaped and includes a wedging tongue 26 having engaging teeth 28 on an upper surface thereof. Wedging tongue 26 engages and wedges strap 12 against an upper interior surface 30 (FIG. 3) of housing member 16 to secure the strap within the buckle. The forward end 32 of wedging tongue 26 also wedges strap 12 against an interior transverse surface 34 of housing 16 to assist in securing the strap within the buckle. Engaging teeth 28 facilitate engagement of strap 12 with wedging member 18 to prevent sliding movement of the strap within the buckle after the buckle is in the secured position.

Wedging member 18 also includes opposed resilient latching legs 36. Each latching leg includes a detent 38 which engage correspondingly positioned and dimensioned opposed recesses 40 formed in housing 16 to form a tight snap lock fit between the two components. Wedging member 18 also includes a slotted opening 42 in transverse side 44. Slotted opening 42 receives strap 12 so that wedging member 18 is positioned on the strap during the tensioning procedure.

The components of buckle 14 are preferably fabricated from synthetic absorbable materials including polymers or copolymers of glycolide, lactide, trimethylene carbonate, lactone, dioxanone, caprolactone or blends thereof. This is a significant aspect of the present invention in that the buckle will eventually be absorbed within the body, unlike conventional metallic buckle assemblies utilized for sternum closure, which metallic buckles the scope of permanently remain within the body and in many instances become detached from strap 12 so as to "float" about the thoracic cavity. It is also within the present invention for buckle 14 to be fabricated from nonabsorbable materials including polycarbonate, polyesters, polyethylene, polyamides, polyvinyl chlorides, polypropylenes, polytetrafluoroethylene, polysulfones, acrylics and polypropylene. It is also possible for buckle 14 to be fabricated from a combination of such absorbable and non-absorbable materials.

Figure 4:
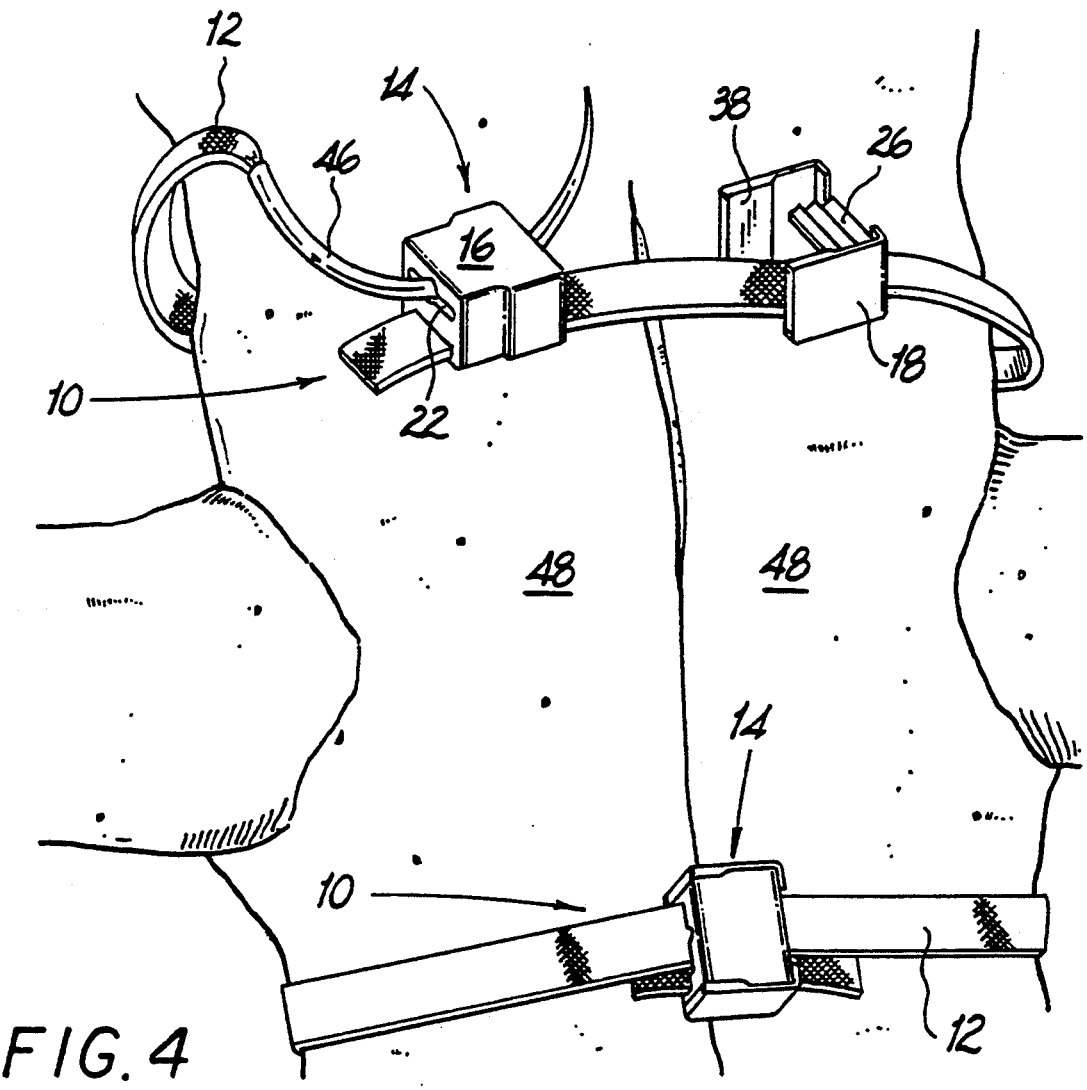
FIG. 4 is a perspective view of the strap buckle of FIG. 1 in a closed looped configuration about the sternum.

As shown in FIG. 4, strap 12 may have a surgical needle 46 attached at its free end to assist in penetrating the targeted parasternal location and passing the strap under the sternum and then outwardly at an opposite parasternal location. A curved needle is appropriate for sternum closure and may be securely attached to strap 12 by conventional methods. The end portion of strap 12, which is to be attached to needle 46, may be tapered to facilitate the needle-attachment process.

Further understanding of the strap assembly 10 of the present invention will be realized from the description provided of the use of same in securing split portions of a sternum together after a sternotomy.

FIG. 4 illustrates two strap assemblies positioned about split sternum portions 48. A first strap assembly 10 is shown positioned about an upper section of the sternum, with buckle 14 in the non-secured position. A second strap assembly 10 is shown positioned about a lower section of the sternum, with the buckle 14 in the secured position.

The application of strap assembly 10 around sternum portions 48 to effect sternum closure is accomplished by grasping a first end of strap 12, with needle 46 attached thereto, and inserting the needle with attached strap through intercostal tissue between adjacent ribs at a first side of the sternum and then maneuvering the needle under both sternum portions 48 to an opposite parasternal location where it is exposed from the intercostal tissue between the ribs at a second side of the sternum. The needle with attached strap 12 is pulled from the sternum location until a sufficient working length of the strap is provided. The needle is inserted through slotted opening 22 of housing 16 preferably within the region defined between arcuate portions 24 and passed through channel 20 of housing 16. The surgeon removes the slack in strap 12 and continues pulling on the strap in a tensioning direction. Once strap 12 is tightened to a desired tension, wedging member 18 is slid along the strap and driven, preferably with a surgical instrument, into channel 20 of housing member 16 to mount the wedging member 18 to the housing. In this mounted position, wedging member 18 securely wedges the strap against interior upper surface of housing 10. The strap is also secured between forward end 32 of tongue 26 and the interior transverse surface 34. Teeth 28 engage the strap to prevent slippage of the strap through housing.

Figure 5:
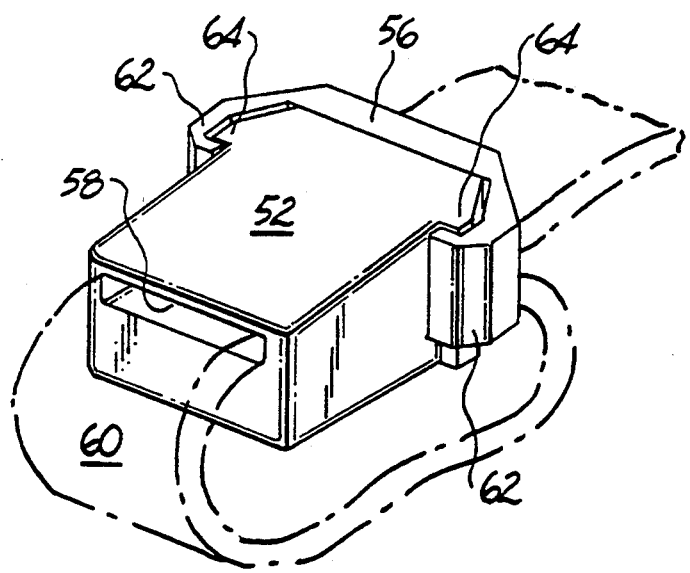
FIG. 5 is a perspective view of an alternative embodiment of the present invention.
Figure 6:
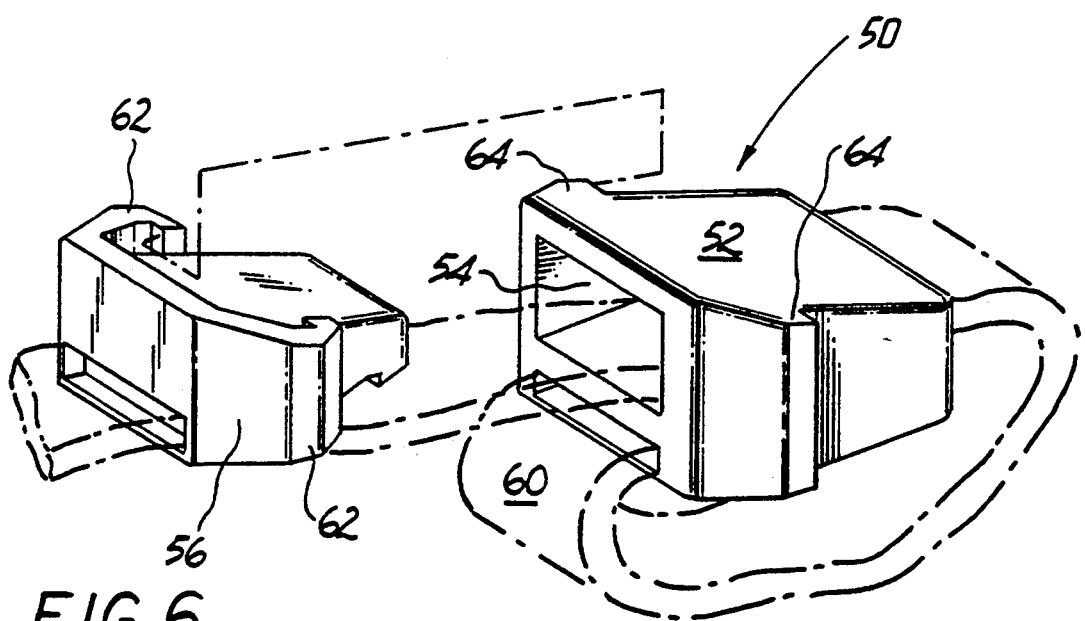
FIG. 6 is a perspective view with parts separated of the embodiment of FIG. 5.
Figure 7:
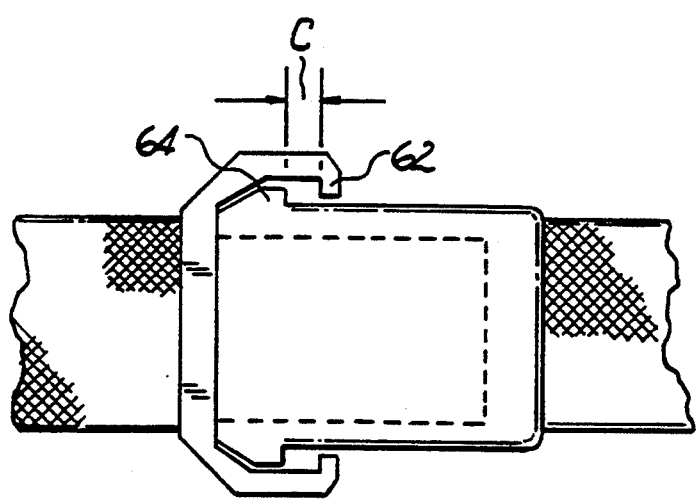
FIG. 7 is a top plan view of the buckle member of FIG. 5.

Referring now to FIGS. 5–7, there is illustrated an alternative buckle assembly of the present invention. Buckle 50 includes housing member 52 having longitudinal channel 54 extending therethrough. Channel 54 defines an enlarged opening in a forward end of housing 52 strategically dimensioned to receive wedging member 56 therein and a second opening 58 in a rear surface of the housing. Second opening 58 is dimensioned to receive the free end of strap 60 which is passed through channel 54 during strap tensioning about the sternum halves.

Wedging member 56 is inserted within channel 54 of housing 52 and is mounted to the housing by the engagement of resilient locking hooks 62 extending from each side of the wedging member and correspondingly positioned and dimensioned projections 64 extending from the sides of housing 52. Locking hooks 62 and projections 64 are particularly dimensioned such that a slight clearance "c" (FIG. 7) exists between the hooks and projections. This clearance permits slight reciprocal movement of wedging member 56 within channel 54 of housing 52 from a non-strap securing position (FIG. 8) to permit passage of the free end of strap 12 through housing 52, i.e., in a tightening direction, to a strap securing position (FIG. 9) wherein the forward end 68 of wedging member 56 secures the strap against transverse bearing surface 70.

It is to be noted that wedging member 56 is mounted to housing 52 prior to application about the tissue portions, i.e., the buckle 50 is preassembled.

Figure 8:
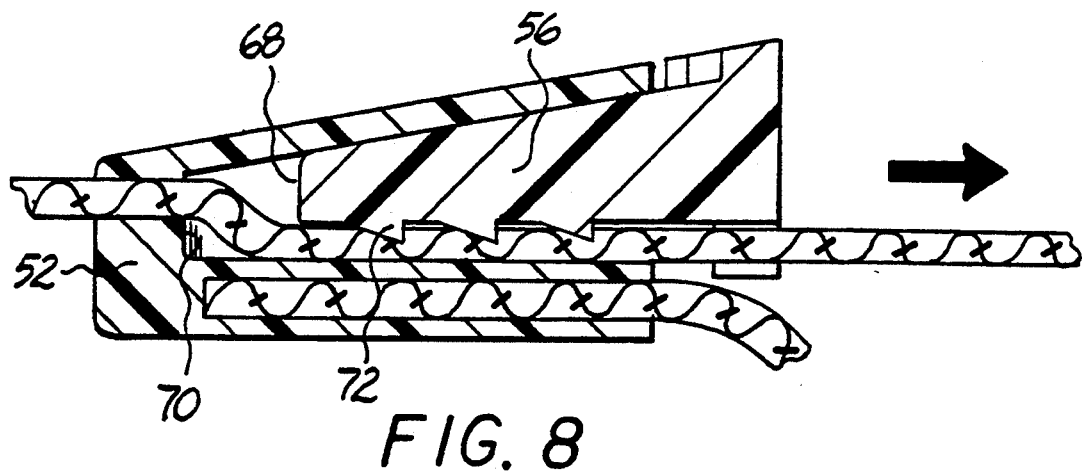
FIG. 8 is a side view in cross-section of the buckle member of FIG. 5 illustrating the non-secured position of the buckle member.
Figure 9:
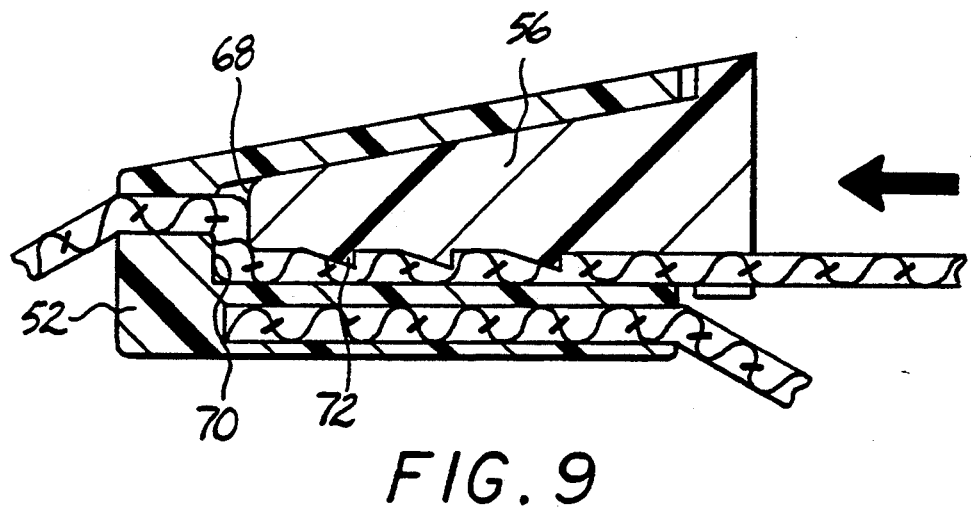
FIG. 9 is a side view in cross-section of the buckle member of FIG. 5 illustrating the secured position of the buckle member with the wedging member securely engaging the strap received within the buckle.

Referring now to FIGS. 8 and 9, wedging member includes engaging teeth 72 on a lower surface thereof to facilitate frictional engagement of the free end of strap 60. Engaging teeth 72 are preferably angularly oriented as shown to permit the free end of strap 60 to pass in one direction, i.e., a strap tensioning direction, as indicated by the arrow in FIG. 8, within channel 54 of housing 52 when the strap is being tightened about the tissue portions while engaging and preventing the strap end portions from passing in a strap loosening direction during tensioning of the strap about the tissue portions.

Wedging member 56 longitudinally moves to its strap securing position in response to the tensional forces exerted on strap 60 during tightening thereof about the tissue portions. In particular, as strap 60 is tightened about the tissue portions the strap generates internal reacting forces or clamping forces which oppose the tensional forces exerted on the strap. These reacting forces effect movement of strap 60 towards its unstressed condition, i.e., causing the free ends of the strap to move in a loosening direction, (as indicated by the arrow in FIG. 9) when the strap end portion is released. During this movement, angularly oriented strap engaging teeth 72 on the lower surface of clamp engage and penetrate the strap ends. Further sliding movement of the strap end in the loosening direction causes wedging member 56 to longitudinally move in direction indicated by the arrow in FIG. 9, due to the engagement of teeth 72 with the strap end, to its secured position. In this position, forward bearing surface 68 of the wedging member 56 securely wedges the strap end portion against bearing surface 70 of housing 52. In addition, wedging member 56 is driven downwardly against strap 60 as the wedging member is advanced to its forward strap securing position due to the corresponding slanted configuration of the upper plate and upper surfaces of housing and wedging members 52,56, respectively. Thus, it is to be appreciated that the tensional forces exerted on strap 60 during tightening thereof about the sternum effect securement of buckle 50. Generally, the amount of tensional forces needed to generate a clamping force sufficient to maintain wedging member 56 in the secured position is minimal.

Figure 10:
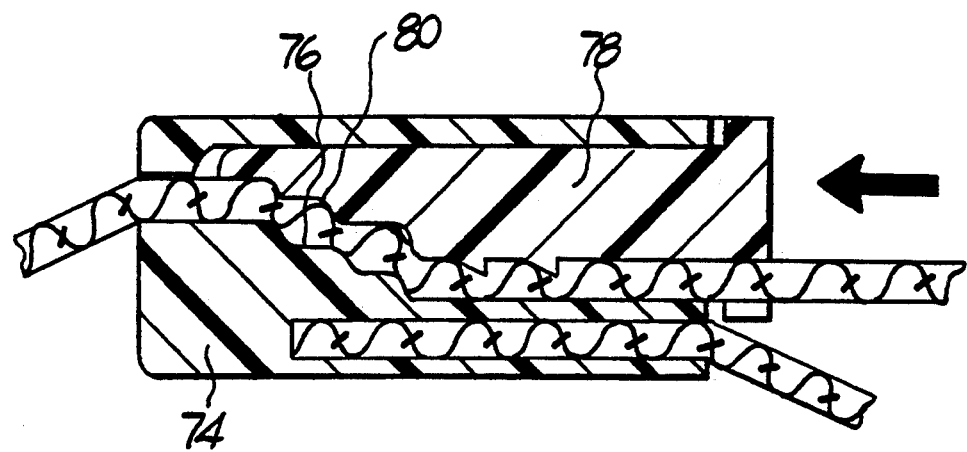
FIG. 10 is a side view in cross-section of another alternative embodiment illustrating corresponding stepped wedging regions of the wedging and housing members.

Referring now to FIG. 10, there is illustrated a side view in cross-section of another preferred embodiment of the buckle of the present invention. This embodiment is similar in most respects to the embodiment described in FIGS. 5-9 except that housing 74 includes a bearing surface 76 having a stepped configuration. Similarly wedging member 78 includes a stepped bearing surface 80 formed in its forward portion which complements the stepped region of bearing surface 76. In the secured position of the buckle, the strap member is secured between the stepped regions 76, 80 of each component. The advantage of such configuration is that the wedging surfaces increase the amount of wedging contact on the strap between wedging member 78 and housing 74. Stepped regions 76, 80 also alter the path in which the free end of the strap is received within housing 74, and, as such, impede sliding movement of the strap end portion within the buckle. FIG. 10 illustrates wedging member in the secured position.

Figure 11:
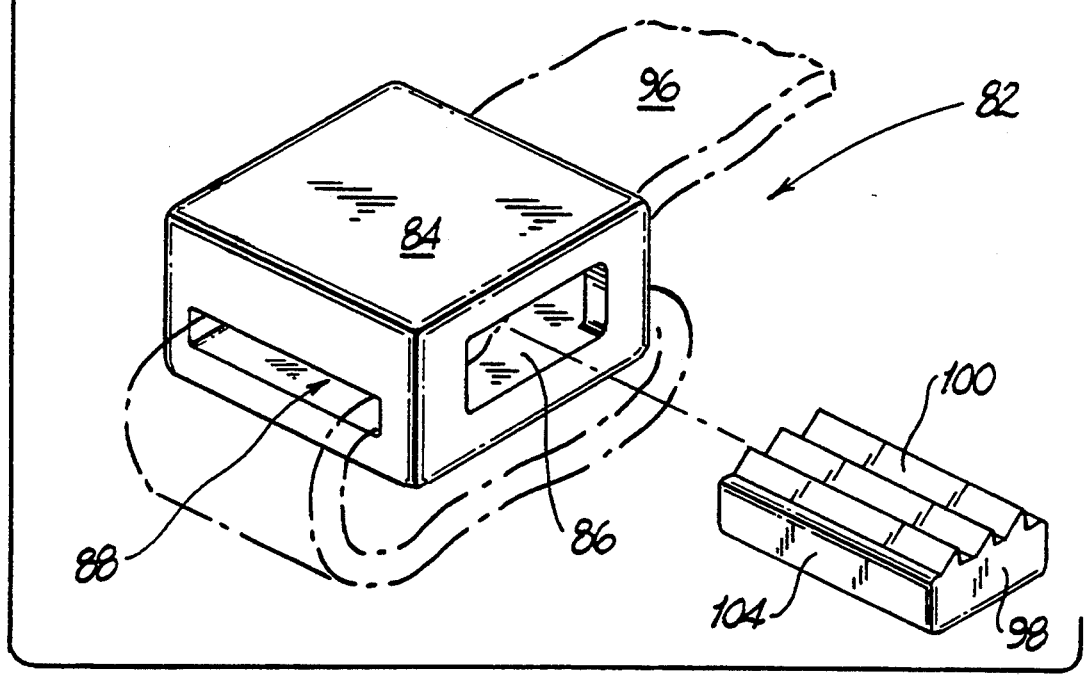
FIG. 11 is a perspective view with parts separated of another alternative buckle of the present invention.
Figure 12:
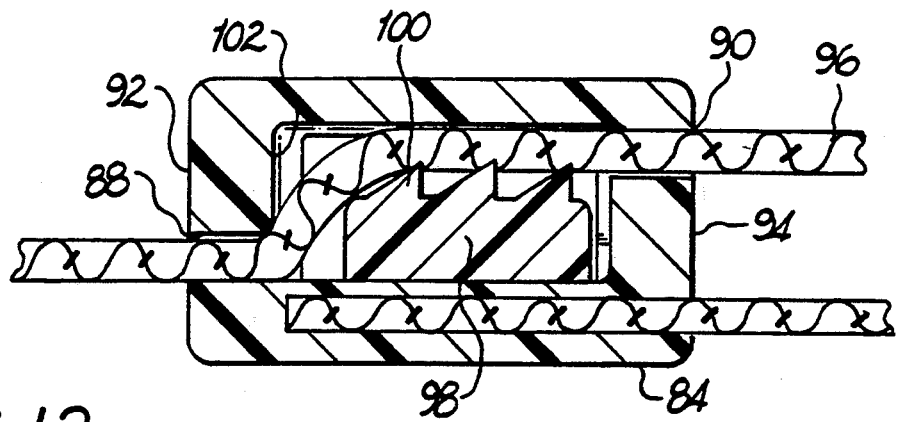
FIG. 12 is a side view in cross-section of the buckle member of FIG. 11 illustrating the non-secured position of the buckle member.
Figure 13:
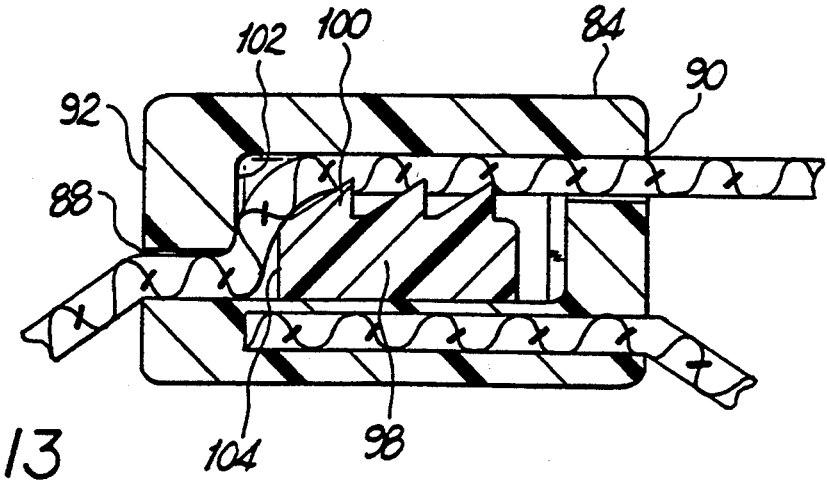
FIG. 13 is a side view in cross-section of the buckle member of FIG. 11 illustrating the secured position of the buckle member with the wedging member securely engaging the strap received within the buckle.

Referring now to FIG. 11-13, there is illustrated a perspective view of an alternative embodiment of the buckle of the present invention. Buckle 82 includes housing 84 defining a partial longitudinal channel 86 and openings 88, 90 formed in forward and rear plates 92, 94 respectively. Openings 88, 90 communicate with partial longitudinal channel 86, and, form in combination with the channel, a passageway for reception and passage of the free end of strap 96. The other end of strap is attached to housing 92 by insert molding or any other conventional means suitable for this purpose.

A bar clamp or wedging member 98 is housed within channel 86 of housing 84 and is reciprocally moveable within the channel from a non-strap securing position to a securing position. Wedging member includes teeth 100 which are angularly oriented in a similar manner of the teeth described in the embodiment of FIGS. 5-9.

To secure the strap assembly about the tissue portions, the free end of strap 96 is introduced within opening 88 and passed between the upper surface of housing 84 and wedging member 98. Strap 96 is tightened about the tissue portions to remove most of the slack. Due to the angular orientation of teeth 100 strap 96 may pass in a tensioning direction without engaging the teeth. Once the desired tension is achieved, the free end of strap 96 is released which thereby causes movement of the strap in a loosening direction and engagement of the strap with teeth 100. Wedging member 98, due to its engagement with strap 96, is driven towards inner bearing surface 102 of where it securely wedges the strap against a forward bearing surface 104 of the wedging member 98 and the inner bearing surface 102. Strap 96 is also wedged against upper interior surface. FIG. 13 shows the secured position of wedging member 98.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A strap assembly for surgical repair of split portions of tissue to retain the tissue portions in adjacent contacting relation during healing, which comprises:
    a flexible elongated strap member dimensioned to be looped about split portions of tissue; and
    buckle means for securing said strap member in a looped tensioned condition about the split tissue portions, said buckle means comprising:
        housing means including first and second opposing end walls, each said end wall including an opening formed therein, said openings defining a passage for reception of said strap member; and
        wedging means slidably receivable within said housing means and adapted to advance into engagement with said strap member to securely wedge said strap member against one of said first and second end walls of said housing means.

2. The strap assembly according to claim 1 further comprising means for mounting said wedging means to said housing means.

3. The strap assembly according to claim 2 wherein said wedging means comprises strap engaging means disposed on at least one of an upper and lower surface thereof to facilitate engagement with said strap member.

4. The strap according to claim 1 wherein a first end portion of said strap member is connected to said housing means.

5. The strap assembly according to claim 1 wherein said
    wedging means is moveable within said housing means between a non-strap securing position and a strap securing position, said wedging means moving to said strap securing position in response to the tensional forces exerted on said strap member, said wedging means securely wedging said strap member against said one of said first and second end walls of said housing means when in said strap securing position.

6. The strap assembly according to claim 5 wherein said wedging means comprises strap engaging means disposed on at least one of an upper and lower surface thereof, said strap engaging means facilitating engagement of said strap member with said wedging means.

7. The strap assembly according to claim 6, wherein said strap engaging means is angularly oriented in a manner to permit advancement of said strap member through said passage in a strap tightening direction while engaging said strap member when said strap member moves through said passage in a strap loosening direction, wherein engagement of said strap member by said strap engaging means during movement of said strap member in the strap loosening direction effects movement of said wedging means to said strap securing position.

8. The strap assembly according to claim 5 further comprising means for mounting said wedging means within said passage of said housing means, said mounting means permitting reciprocal movement of said wedging means between said non-strap securing position and said strap securing position.

9. The strap assembly according to claim 1 wherein said wedging means further comprises a stepped region at a forward portion thereof, said stepped region corresponding to a stepped region formed in said one of said first and second opposing end walls of said housing means, said stepped regions of said wedging means and said housing means securely wedging said strap member therebetween when said wedging means is in said strap securing position.

10. The strap assembly according to claim 1 wherein said strap member comprises nonabsorbable synthetic fibers selected from the group consisting of polycarbonate, polyesters, polybutylene terephthalate, polyethylene terephthalate, polyethylene, polyamides, polyvinyl chloride, polypropylenes, polytetrafluoroethylene and polysulfones.

11. The strap assembly according to claim 1 wherein said strap member comprises bioabsorbable fibers selected from the group consisting of catgut and synthetic materials including polymers and copolymers of lactide, glycolide, dioxanone, caprolactone and trimethylene carbonate.

12. The strap assembly according to claim 1 further comprising a surgical needle attached to an end portion of said strap member.

13. The strap assembly according to claim 1 wherein said buckle means comprises a bioabsorbable material selected from the group consisting of polymers and copolymers of lactide, glycolide, dioxanone, caprolactone and trimethylene carbonate.

14. The strap assembly according to claim 1 wherein said strap member and said buckle means are adapted to retain split portions of a human sternum in contacting relation during healing.

15. A strap assembly for surgical repair of split portions of tissue to retain the tissue portions in adjacent contacting relation during heading, which comprises:
an elongated strap member; and
buckle means for securing said strap member about split portions of tissue, said buckle means comprising:
housing means defining a longitudinal channel therethrough for reception of said strap member;
wedging means insertable within said longitudinal channel of said housing means to securely wedge said strap member against at least one bearing surface of said housing means; and
means for mounting said wedging means within said longitudinal channel of said housing means, said mounting means comprising first and second locking hooks extending from opposed sides of said wedging means, said first and second locking hooks securely engaging correspondingly dimensioned and positioned projections extending from opposed sides of said housing means.

16. The strap assembly according to claim 15 wherein said strap member and said buckle means are each fabricated from a bioabsorbable material selected from the group consisting polymers and copolymers of lactide, glycolide, dioxanone, caprolactone and trimethylene carbonate.

17. A strap assembly for surgical repair of split portions of tissue to retain the tissue portions in adjacent contacting relation during healing, which comprises:
an elongated strap member; and
a buckle member for securing said strap member in a looped tensioned condition about the tissue portions, said buckle member comprising:
a housing member defining a longitudinal channel therethrough for reception of said strap member;
a wedging member disposed within said longitudinal channel; and
means for mounting said wedging member to said housing member to permit reciprocal longitudinal movement of said wedging member within said longitudinal channel between a non-strap securing position to permit passage of said strap member through said longitudinal channel and a strap securing position wherein said wedging member securely wedges said strap member against at least one bearing surface of said housing member, said mounting means comprising first and second locking hooks extending from opposed sides of said wedging member, said first and second locking hooks engaging correspondingly dimensioned and positioned projections extending from opposed sides of said housing member to mount said wedging member to said housing member, said locking hooks and said projections defining a clearance therebetween to permit reciprocal movement of said wedging member between said non-strap securing position and said strap securing position.

18. The strap assembly according to claim 17 wherein said strap member and said buckle member are each fabricated from a bioabsorbable material selected from the group consisting of polymers and copolymers of lactide, glycolide, dioxanone, caprolactone and trimethylene carbonate.

19. A strap assembly to be looped about split portions of tissue to retain the tissue portions in adjacent engaged relation to promote healing thereof, which comprises:
a flexible generally planar strap member having at least an upper and a lower substantially planar surface and being dimensioned to be looped about split portions of tissue; and
buckle means including housing means defining a channel extending therethrough and wedging means mounted within said channel of said housing means and movable therewithin between a non strap securing position and a strap securing position, said wedging means having strap engaging means disposed on at least one of an upper and lower surface thereof, said strap engaging means angularly oriented to permit advancement of said strap member in a strap tightening direction while engaging one of said upper and lower planar surfaces of said planar strap member when said strap member moves through said channel in a strap loosening direction, wherein engagement of said strap member by said engagement means during movement of said strap member in the strap loosening direction effects movement of said wedging means to said strap securing position.

20. The strap assembly according to claim 19 wherein said wedging means comprises a bar-like clamp slidably housed within said channel of said housing means.

21. The strap assembly according to claim 19 wherein said strap member and said buckle means are each fabricated from a bioabsorbable material selected from the group consisting of polymers and copolymers of lactide, glycolide, dioxanone, caprolactone and trimethylene carbonate.

22. A method for repairing split portions of tissue, comprising the steps of:
providing at least one strap assembly including a strap member and buckle means, said buckle means including housing means defining a longitudinal channel for reception of said strap member and wedging means dimensioned to be received within said longitudinal channel;
looping said strap member around the tissue portions;
inserting said strap member through said longitudinal channel in said buckle means;

tightening said strap member about the tissue portions in a manner to attach the tissue portions in an adjacent engaged relation; and inserting said wedging means within said longitudinal channel of said housing means to securely wedge said strap member against a bearing surface of said housing means.

23. A method for repairing split portions of tissue, comprising the steps of:

providing at least one strap assembly including a strap member and buckle means, said buckle means including housing means defining a longitudinal channel for reception of said strap member and wedging means slidably housed within said longitudinal channel from a non-strap securing position to a strap securing position in response to tensional forces exerted on said strap member during tensioning thereof about the tissue portions, said wedging means comprising strap engaging means for engaging said strap member;

looping said strap member about the tissue portions;

introducing said strap member into said longitudinal channel of said housing means;

tensioning said strap member about the tissue portions in a manner to attach the tissue portions in an adjacent engaged relation; and releasing said strap member such that said strap engaging means of said wedging means engages said strap member to cause said wedging means to move to said strap securing position wherein said wedging means securely wedges said strap member against at least a transverse bearing surface of said housing means to secure said strap member in a looped tensioned condition about the split tissue portions.

24. The method according to claim 23 wherein said step of looping said strap member comprises looping said strap member about split portions of a human sternum for surgical repair of the sternum.

25. A strap assembly to be looped about split portions of tissue to retain the portions in adjacent engaged relation to promote healing thereof, which comprises:

a flexible strap member; and a buckle member, comprising:

a housing member defining a longitudinal channel dimensioned for reception and passage of said strap member therethrough, said housing member including a transverse bearing surface and a longitudinal bearing surface; and a wedging member positionable within said longitudinal channel of said housing member and dimensioned and configured to securely wedge said strap member against said transverse bearing surface of said housing member and said longitudinal bearing surface of said housing member.

26. The strap assembly according to claim 25 wherein said strap member and said buckle member are each fabricated from a bioabsorbable material selected from the group consisting of polymers and copolymers of lactide, glycolide, dioxanone, caprolactone and trimethylene carbonate.

27. A strap assembly for surgical repair of split portions of tissue to retain the tissue portions in adjacent contacting relation during healing, which comprises:

a flexible elongated strap member dimensioned to be looped about split portion of tissue; and a buckle member for securing said strap member in a looped tensioned condition about the split tissue portions, said buckle member comprising:

a housing member including a channel therethrough for reception of said strap member and at least one bearing surface, said at least bearing surface defining a stepped region; and a wedging member slidably receivable within said channel of said housing member, said wedging member including a stepped region at one end portion thereof generally corresponding in dimension and configuration to said stepped region of said housing member, said wedging member adapted to advance into engagement with said strap member such that said strap member is securably wedged between said stepped region of said wedging member and said stepped region of said housing member.

28. A strap assembly to be looped about split portions of tissue to retain the portions in adjacent engaged relation to promote healing thereof, which comprises:

a flexible strap member; and a buckle member, comprising:

a housing member including first and second opposed end walls and at least one connecting wall interconnecting said first and second end walls, each said end wall having an opening formed therein, said openings defining a passage through said housing member for reception of said strap member, said housing member further including at least one bearing surface, said at least one bearing surface being angularly oriented relative to said at least one connecting wall; and a wedging member positionable within said housing member and dimensioned and configured to securely wedge said strap member against said at least one bearing surface of said housing member.

29. A strap assembly to be looped about split portions of tissue to retain the portions in adjacent engaged relation to promote healing thereof, which comprises:

a flexible strap member; and a buckle member, comprising:

a housing member including first and second opposed end walls and a connecting wall interconnecting said first and second end walls, each said end wall having an opening formed therein, said openings defining a passage through said housing member for reception of said strap member; and a wedging member positionable within said housing member and dimensioned and configured to securely wedge said strap member against one of said first and second opposed end walls and against said at least one connecting wall.

* * * * *